United States Patent [19]
Shelton et al.

[11] Patent Number: 5,325,478
[45] Date of Patent: Jun. 28, 1994

[54] METHOD FOR DISPLAYING INFORMATION FROM AN INFORMATION BASED COMPUTER SYSTEM

[75] Inventors: Richard Shelton, Mesa; Audree Thurman, Phoenix; Stanley Person; Ronald Norden-Paul, both of Mesa, all of Ariz.

[73] Assignee: Emtek Health Care Systems, Inc., Tempe, Ariz.

[21] Appl. No.: 407,836

[22] Filed: Sep. 15, 1989

[51] Int. Cl.⁵ .............................................. G06F 15/16
[52] U.S. Cl. .................... 395/148; 395/145; 395/155
[58] Field of Search ............... 364/518, 521, 522, 523, 364/200 MS File, 900 MS File; 340/747, 750; 395/155, 161, 148, 145

[56] References Cited
U.S. PATENT DOCUMENTS

| | | | |
|---|---|---|---|
| 4,591,974 | 5/1986 | Dornbush et al. | 364/200 |
| 4,891,771 | 1/1990 | Edel et al. | 364/523 |
| 4,893,256 | 1/1990 | Rutherford et al. | 364/518 |
| 4,926,349 | 5/1990 | Thor | 364/523 |

FOREIGN PATENT DOCUMENTS 0211151 2/1987 European Pat. Off. ...... G06F 15/20

OTHER PUBLICATIONS

"POMS—Patient Data Management System—System Description" Hewlett Packard (Jan. 1982).
"POMS—Patient Data Management System—Clinical User's Guide" Hewlett Packard (Jan. 1982).
"ULTICARE"—a bedside patient care information system" Health Data Sciences (Oct. 1984).
John E. Brimm, MD, "Computers in Critical Care", Critical Care Nursing Quarterly 1987; 9(4): 53-63.

Primary Examiner—Phu K. Nguyen
Attorney, Agent, or Firm—Walter W. Nielsen; Raymond J. Warren

[57] ABSTRACT

Information is displayed from an information based computer system which comprises the consolidation of information from various object instances onto a single form. Changes or corrections to data values are maintained in a historical record. When the form is displayed, options are provided indicating whether there are older or newer data values resulting from changes or corrections being made to the original data value.

13 Claims, 13 Drawing Sheets

| SECTIONS: | FLOWSHEET | ASSESSMENT | NCP | KARDEX | | | |
|---|---|---|---|---|---|---|---|
| FORMS: | ORDER SHEET | ORDER HISTORY | | | | | |
| | ORDER TEXT *116* | | | STATUS | ORDER DATE / TIME | | |
| MEDS | DIGOXIN 0.125 mg IV qd | | | ACTIVE | 03/24 | 0900 | JB / LN |
| | MORPHINE SULFATE 1-5 mg IV q4h PRN SEVERE PAIN | | | ACTIVE | 03/24 | 0900 | JB / LN |
| | AMPICILLIN 500 mg IVPB q6h | | | ACTIVE | 03/24 | 0900 | JB / LN |
| | VALIUM TABLET 5 mg ORAL qd  *123 124*  *120*<br>PRN RESTLESSNESS  *122*<br>*121*  *125* | | | NOW | 03/24 | 0900 | JB / LN |
| IV'S | 500cc NS FLUSH SWAN-GANZ 1000 UNITS HEPARIN | | | ACTIVE | 03/24 | 0900 | JB / LN |
| | 250cc D5W LEFT ARM 50 mg NIPRIDE | | | ACTIVE | 03/24 | 0900 | JB / LN |
| | 500cc D5W TKO LEFT ARM | | | ACTIVE | 03/24 | 0900 | JB / LN |
| LAB | H & H | | | ACTIVE | 03/24 | 0900 | JB / LN |
| | LYTES | | | ACTIVE | 03/24 | 0900 | JB / LN |
| | EKG MCL1 | | | ACTIVE | 03/24 | 0900 | JB / LN |

Patient: DOE, JOHN K. — M 08/19/40 — 01-56-16 — 9NB — ALLERGIES: CODEINE

*102* *101* *104* *103* *111* *112* *113* *100* *105* *106*

[NEW ORDER]    [SIGN]

| | | 7/7 10:30 | 7/7 11:00 | 7/7 11:30 | 7/7 12:00 | 7/7 12:30 | 7/7 13:00 |
|---|---|---|---|---|---|---|---|
| VITALS 453A | | 453C | | 453C | 453C | | |
| 454A | HEART RATE 453B | 454B | 454C | | 454C | 454C | |
| 455A | BLOOD PRESSURE 454B | 455B | | 455C | | | |
| 456A | TEMP. 455B | 456B | | | | 456C | |
| LABS 457A | RESPIRATION RATE 456B | 457B | 457C | | | | |
| 458A | CBC HGB 457B | 458B | | | 458C | | |
| 459A | CBC HCT 458B | 459B | | 459C | | | 459C |
| 460A | K+ 459B | 460B | 460C | | | 460C | |
| 461A | Na 460B | 461B | | | 461C | | |
| 462A | BUN 461B | 462B | | 462C | | | |
| | CREAT 462B | | | | | | |

FIG. 5

|  | | 7/7 10:30 | 7/7 11:00 | 7/7 11:30 | 7/7 12:00 | 7/7 12:30 | 7/7 13:00 |
|---|---|---|---|---|---|---|---|
| 453A VITALS | | 453B | | 453C | 453C | | |
| 454A | HEART RATE | 454B | 454C | | 454C | 454C | |
| 455A | BLOOD PRESSURE | 455B | | | | | |
| 456A | TEMP. | 456B | | 455C | | | |
| | RESPIRATION RATE | | | | | 456C | |
| LABS 457A | CBC HGB | 457B | 457C | | | | |
| 458A | CBC HCT | 458B | 465 | | | 458C | |
| 459A | K+ | 459B | 459C | | | | 459C |
| 460A | Na | 460B 460C | 460C | | | 460C | |
| 461A | BUN | 461B | | | 461C | | |
| 462A | CREAT | 462B | | 462C | | | |

(1) MAKE ENTRY
(2) CORRECT ENTRY
(3) SHOW DETAIL
(4)
(5)
(6)
(7)         470

FIG. 6

| SECTION: | FLOWSHEET | —501 |
|---|---|---|
| FORM: | LABS | —502 |
| PARAMETER: | CBC | —503 |
| SUBPARAMETER: | HGB | —504 |

PARAMETER DESCRIPTION:

Complete Blood Count —505A

HemoGloBin —505B

SUBPARAMETER VALUE: ________ —506

SAMPLE REF NO.: ________ —507

TIME SAMPLE DRAWN: ________ —508

TIME SAMPLE RUN: ________ —509

TIME TESTS REPORTED: ________ —510

ANNOTATION: ________ —511

```
┌─────────────────────────────────────────────────┐
│           COMPLETE BLOOD COUNT                  │
│                  CBC                            │
├─────────────────────────────────────────────────┤
│                                                 │
│   SAMPLE REF NO.: _______________________ —601  │
│                                                 │
│  ⎧ MEASURED VALUES:                             │
│  ⎪                                              │
│  ⎪    WBC — WHITE BLOOD CELL COUNT: ____ —602   │
│  ⎪                                              │
│  ⎪    RBC — RED BLOOD CELL COUNT:    ____ —603  │
│ 611                                             │
│  ⎨    HGB — HEMOGLOBIN:               ____ —604 │
│  ⎪                                              │
│  ⎪    MCV — MEAN CELL VOLUME:         ____ —605 │
│  ⎪                                              │
│  ⎩    PLT — PLATELETS:                ____ —606 │
│                                                 │
│  ⎧ CALCULATED VALUES:                           │
│  ⎪                                              │
│  ⎪    HCT — HEMATOCRIT                ____ —607 │
│ 612                                             │
│  ⎨    MCH — MEAN CELL HEMOGLOBIN:    ──── —608  │
│  ⎪                                              │
│  ⎩    MCHC — MEAN CELL HEMOGLOBIN    ____ —609  │
│                      CONCENTRATION:             │
│                                                 │
│   ANNOTATION: ______________________       —610 │
│                                                 │
│   ______________________________________        │
└─────────────────────────────────────────────────┘
                        ↑
                       600
```

FIG. 8

```
┌─────────────────────────────────┐
│         LAB TEST ORDER          │
├─────────────────────────────────┤
│                                 │
│  DATE/TIME ORDERED: ______ 701  │
│                            702  │
│  ORDERING M.D.:     ______      │
│                                 │
│  TEST ORDERED:                  │
│         CBC: ____  ⎫            │
│          K+: ____  ⎬  703       │
│          NA: ____  ⎪            │
│         BUN: ____  ⎪            │
│       CREAT: ____  ⎭            │
│                           704   │
│  SAMPLES DRAWN BY:  ______      │
│                           705   │
│  TIME SAMPLE DRAWN: ______      │
│                           706   │
│  SAMPLE REF. NO.:   ______      │
│                           707   │
│  ANNOTATION: _____________      │
│                                 │
│  _____________________________  │
└─────────────────────────────────┘

| | | | 101 |
|---|---|---|---|
| 102 | DOE, JOHN K. | 9NB | |
| | M 08/19/40 01-56-16 | ALLERGIES: CODEINE 103 | 104 |

SECTIONS: FLOWSHEET [ORDERS] ASSESSMENT NCP KARDEX

FORMS: [ORDER SHEET] ORDER HISTORY

111

| | ORDER TEXT 116 | STATUS | ORDER DATE / TIME 112 | 113 |
|---|---|---|---|---|
| MEDS | DIGOXIN 0.125 mg IV qd | ACTIVE | 03/24 0900 | JB / LN MD |
| | MORPHINE SULFATE 1-5 mg IV q4h PRN SEVERE PAIN | ACTIVE | 03/24 0900 | JB / LN |
| | AMPICILLIN 500 mg IVPB q6h | ACTIVE | 03/24 0900 | JB / LN |
| | 121 ⌐VALIUM TABLET ¯5 mg¯ ORAL qd┐ 123 124  120 125 ⌐PRN RESTLESSNESS ────┘ 122 | NOW 141 | ⌐03/24┐ ⌐0900┐ 140 142 | ⌐JB┐ / LN 150 151 |
| IV'S | 500cc NS FLUSH SWAN— 1000 UNITS HEPARIN | TIVE | 03/24 0900 | JB / LN |
| | 250cc D5W LEFT ARM 50 mg NIPRIDE | TIVE | 03/24 0900 | JB / LN |
| | 500cc D5W TKO LEFT A | TIVE | 03/24 0900 | JB / LN |
| LAB | H & H | TIVE | 03/24 0900 | JB / LN |
| | LYTES | TIVE | 03/24 0900 | JB / LN |
| | EKG MCL1 | TIVE | 03/24 0900 | JB / LN |

MEDICATION ORDER ENTRY
ORDER DATE: 03/24 — 302  301
ORDER TIME: 0900 — 303
ORDERING MD: JB — 304
DRUG NAME: VALIUM TABLET — 305
ROUTE: ORAL — 306
DOSE: 5 mg — 307
FREQUENCY: qd — 308
NUMBER OF DOSES:
START DATE: 03/24 — 309
START TIME: 0900 — 310  311
316  COMMENTS: PRN RESTLESSNESS 314
[OK]  312 — [OLDER] [ORIG]

300

[NEW ORDER]   [SIGN]

| 102 | | DOE, JOHN K. | 9NB |
|---|---|---|---|
| | | M 08/19/40 01-56-16 | ALLERGIES: CODEINE |

SECTIONS: FLOWSHEET [ORDERS] ASSESSMENT NCP KARDEX

FORMS: [ORDER SHEET] ORDER HISTORY

| | ORDER TEXT | STATUS | ORDER DATE / TIME | |
|---|---|---|---|---|
| MEDS | DIGOXIN 0.125 mg IV qd | ACTIVE | 03/24 0900 | JB / LN MD |
| | MORPHINE SULFATE 1-5 mg IV q4h PRN SEVERE PAIN | ACTIVE | 03/24 0900 | JB / LN |
| | AMPICILLIN 500 mg IVPB q6h | ACTIVE | 03/24 0900 | JB / LN |
| | VALIUM TABLET 5 mg ORAL qd PRN RESTLESSNESS | NOW | 03/24 0900 | JB / LN |
| IV'S | 500cc NS FLUSH SWAN— 1000 UNITS HEPARIN | TIVE | 03/24 0900 | JB / LN |
| | 250cc D5W LEFT ARM 50 mg NIPRIDE | TIVE | 03/24 0900 | JB / LN |
| | 500cc D5W TKO LEFT A | TIVE | 03/24 0900 | JB / LN |
| LAB | H & H | TIVE | 03/24 0900 | JB / LN |
| | LYTES | | | |
| | EKG | | | |
| | MCL1 | | | |

MEDICATION ORDER ENTRY

ORDER DATE: 03/24
ORDER TIME: 0900
ORDERING MD: JB
DRUG NAME: VALIUM TABLET
ROUTE: ORAL
DOSE: 5 mg
FREQUENCY: qd
NUMBER OF DOSES:
START DATE: 03/24
START TIME: 0900
COMMENTS:

[OK] [HOME] [NEWER] [OLDER] [ORIG]

[NEW ORDER] [SIGN]

FIG. 12

| | | | | DOE, JOHN K.<br>M 08/19/40 01-56-16 | | 9NB<br>ALLERGIES: CODEINE | |
|---|---|---|---|---|---|---|---|
| SECTIONS: | FLOWSHEET | [ORDERS] | ASSESSMENT | NCP | KARDEX | | |
| FORMS: | [ORDER SHEET] | ORDER HISTORY | | | | | |

| | ORDER TEXT | STATUS | ORDER DATE / TIME | |
|---|---|---|---|---|
| MEDS | DIGOXIN 0.125 mg IV qd | ACTIVE | 03/24 0900 | JB / LN MD |
| | MORPHINE SULFATE 1-5 mg IV q4h PRN SEVERE PAIN | ACTIVE | 03/24 0900 | JB / LN |
| | AMPICILLIN 500 mg IVPB q6h | ACTIVE | 03/24 0900 | JB / LN |
| | VALIUM TABLET 5 mg ORAL qd PRN RESTLESSNESS | NOW | 03/24 0900 | JB / LN |
| IV'S | 500cc NS FLUSH SWAN-1000 UNITS HEPARIN | ACTIVE | 03/24 0900 | JB / LN |
| | 250cc D5W LEFT ARM 50 mg NIPRIDE | ACTIVE | 03/24 0900 | JB / LN |
| | 500cc D5W TKO LEFT A | ACTIVE | 03/24 0900 | JB / LN |
| LAB | H & H | ACTIVE | 03/24 0900 | JB / LN |
| | LYTES | ACTIVE | 03/24 0900 | JB / LN |
| | EKG MCL1 | ACTIVE | 03/24 0900 | JB / LN |

MEDICATION ORDER ENTRY

ORDER DATE: 03/24
ORDER TIME: 0900
ORDERING MD: JB
DRUG NAME: VALIUM TABLET
ROUTE: ORAL
DOSE: 10 mg
FREQUENCY: qd
START DATE: 03/24
START TIME: 0900
NUMBER OF DOSES:
COMMENTS:

[OK] [HOME] [NEWER]

[NEW ORDER]  [SIGN]

METHOD FOR DISPLAYING INFORMATION FROM AN INFORMATION BASED COMPUTER SYSTEM

RELATED INVENTIONS

The present invention is related to the following inventions, all assigned to the assignee of the present invention:

System Control Structure of a Hospital Information System and Method of Using Same, having Ser. No. 116,614, and filed on Nov. 3, 1987, now abandoned;

Clinical Task List with Charting Through the Task List onto Underlying Form and Automatic Updating of Task List, having Ser. No. 268,822, and filed on Nov. 7, 1987 now abandoned; and continued by U.S. Pat. application Ser. No. 07/572,317, now U.S. Pat. No. 5,077,666;

Clinical Task List with Charting onto Underlying Form and Automatic Updating of Task List, having Ser. No. 268,323, and filed on Nov. 7, 1987, now abandoned; continued by U.S. patent application Ser. No. 07/572,315, now U.S. Pat. No. 5,072,383;

Method for Generating Patient-Specific Flowsheets by Adding/Deleting Parameters, having U.S. Pat. No. 4,878,175, issued on Oct. 31, 1989;

Method for Generating a Display, having Ser. No. 322,740, and filed on Mar. 13, 1989;

A Method for Displaying Information from an Information Based Computer System, having Ser. No. 407,979 and filed on Sep. 15, 1989;

Spreadsheet Cell having Multiple Data Fields, having Ser. No. 408,166 and filed on Sep. 15, 1989 now abandoned; and continued by U.S. patent application Ser. No. 07/689,135;

Electronic Data Storage Interface, having Ser. No. 408,178 and filed on Sep. 15, 1989;

Method for Updating Data in a Database, having Ser. No. 408,167 and filed on Sep. 15, 1989 now abandoned;

Method for Storing a Transaction in a Distributed Database System, having Ser. No. 408,164 and filed on Sep. 15, 1989;

A Method of Forming a Spreadsheet Display, having Ser. No. 407,972 and filed on Sep. 15, 1989 now abandoned; and Data Storage Audit Trail, having Ser. No. 409,230 and filed on Sep. 15, 1989 now abandoned, and continued by U.S. patent application Ser. No. 07/980,135.

FIELD OF THE INVENTION

The present invention relates, in general, to a method of displaying information and, more particularly, to a method for displaying information from an information based computer system.

BACKGROUND OF THE INVENTION

The present invention relates to an automated records management system. Such an automatic system has utility, for example, in a hospital based patient record keeping system. Patient record keeping systems are used for maintaining a wide variety of separate, often interrelated, types of medical records concerning patients.

Hand written patient record keeping systems have evolved through many years of careful refinement and enhancement into systems which maintain a detailed manual record of medical information concerning each patient. To meet the needs of different hospital entities (such as doctors, nurses, pharmacy, accounting, laboratory, etc.) a manual record keeping system would require that one bit of information be entered into multiple records.

In a typical manual patient record keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the Laboratory section there may appear forms for chemistry, hematology, blood gas, and microbiology.

In addition, a "flowsheet" chart is usually kept at the patient's bedside. On the "flowsheet" chart there are individual areas for medications records, vital signs, intake/output, laboratory results, and other categories which are dependent upon the patient's affliction, such as intravenous (IV) drips.

The flowsheets are often a type of spreadsheet arranged by a progression of time versus a particular parameter. Each of the time/parameter intersections forms a cell.

Often, the information for one cell in a flowsheet will come from more than one object instance. Therefor, it is desirable to obtain the various pertinent information from object instances and have it displayed on one form. One or more of the fields from the form may then be displayed on a data cell. This is not available in current medical information systems.

Further, because changes/corrections may be made to the object instances via a form, it is necessary that a history of these changes/corrections be maintained. This is also not available in current medical information systems.

In addition, in order to maintain the efficiency of the information displayed in the data cells, it is desirable that only the most current information be displayed.

While only the most recent information is desired, it is necessary to indicate whether there have been changes in the data being displayed. If is also desirable to permit the user to view the information as it existed prior to being changed. These items are also not available in current medical information systems.

Accordingly, it is an object of the present invention to provide a spreadsheet cell which overcomes the above deficiencies.

A further object of the present invention is to provide a method for displaying information from an information based computer system which consolidates information from various object instances onto a single form.

Another object of the present invention is to provide a method for displaying information from an information based computer system which maintains an historical record of changes/corrections to information in various data objects and forms.

Still another object of the present invention is to provide a method for displaying information from an information based computer system which displays the most currently available information.

yet another object of the present invention is to provide a method for displaying information from an information based computer system which permits the user to view the information as it existed prior to being changes.

These and other objects and advantages are achieved in accordance with a preferred embodiment of the invention described below.

SUMMARY OF THE INVENTION

A particular embodiment of the present invention consists of a method for displaying information from an information based computer system which comprises the consolidation of information from various related object instances onto a form. The form is then displayed to the user. Changes or corrections to the fields of a form (which relate to attributes of one or more object instance) are maintained in a historical record (audit trail). Only the most recent information is displayed to the user. This display may also have an indicator that changes and/or corrections have been made to the underlying object instances. The original data (prior to being changed/corrected) may also be displayed.

BRIEF DESCRIPTION OF THE DRAWINGS

FIGS. 10–12 show a form and illustrate the tracking of historical changes to the underlying object instances displayed on the form.

DETAILED DESCRIPTION OF THE DRAWINGS

Figure 1:
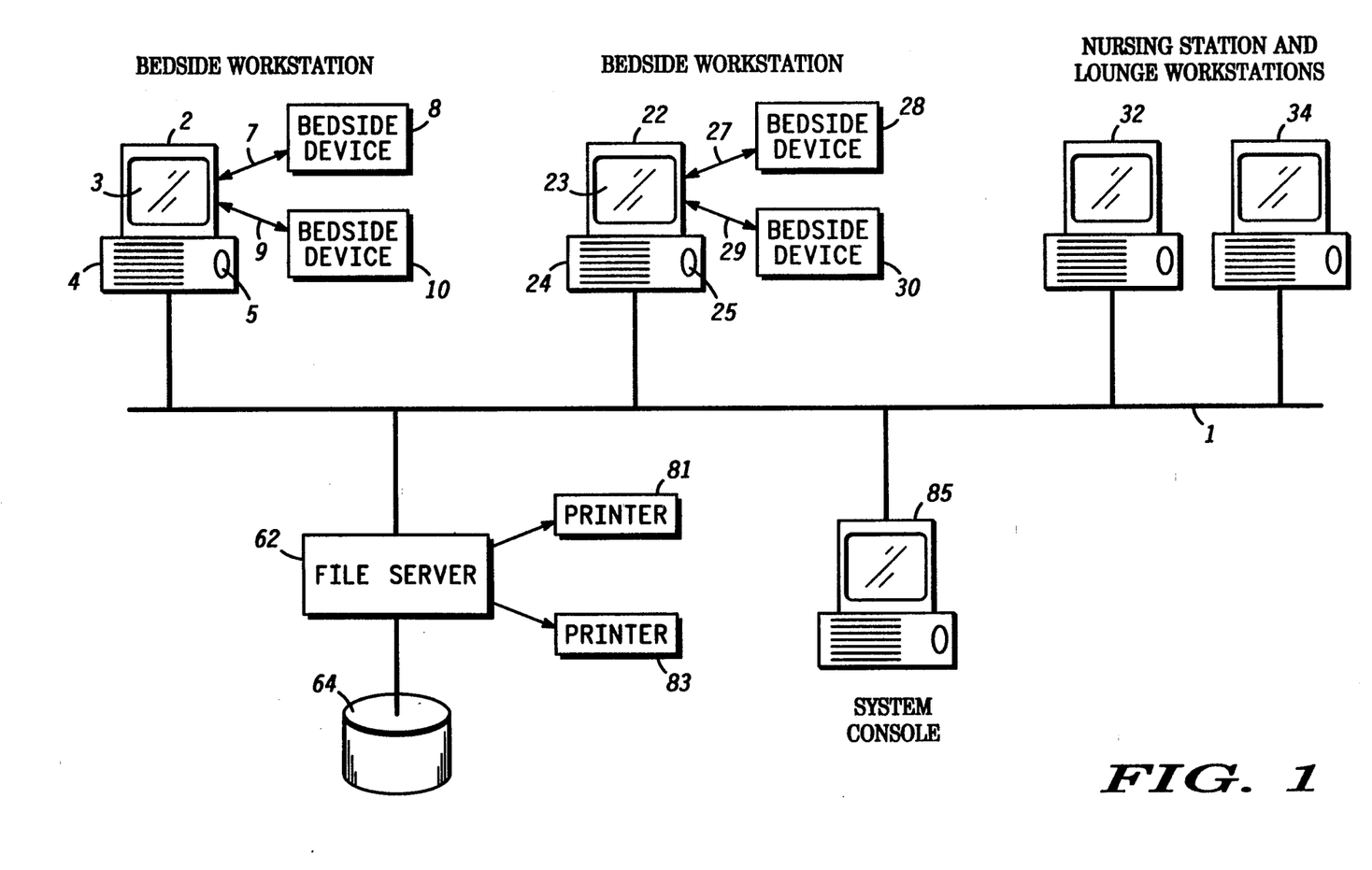
FIG. 1 is a block diagram illustrating a data processing system incorporating the present invention.

Referring initially to the block diagram of FIG. 1, a data processing system is illustrated. FIG. 1 shows a distributed computer system comprising a plurality of workstations 2, 22, 32, 34, and 85 coupled to a local area network (LAN) 1.

The system is typically installed for use in a nursing care unit, such as an intensive care unit, in a hospital or clinic. Terminals 2 and 22 are located at the patient bedside. One terminal may be dedicated to the use of a single patient, or it may be used for multiple patients. Terminals 32 and 34 may be located at a nursing station or nurse/physician lounge area. Terminal 85 is the system console which is used by a system administrator to configure and maintain the system and to provide additional services, such as displaying system status and error messages, archiving, and performing diagnostics.

Each bedside workstation or terminal, such as terminal 2, includes a video display unit with a viewable screen 3 for displaying information to the viewer; a housing 4 containing computing, data storage, and communications equipment and having associated with it a keyboard and pointing device such as a mouse 5; and connections 7 and 9 to one or more bedside devices 8 and 10. Bedside devices 8, 10, 28, and 30 may take the form of patient monitoring equipment suitable for the patient undergoing care, such as an EKG monitor, respiratory monitor, etc. Bedside terminal 22 may be coupled to a different set of bedside devices than those coupled to terminal 2.

The nursing station or lounge terminals 32 and 34, and system 85, may be identical to those used in the patient care unit but without the bedside device connections, or they may comprise slightly different equipment (e.g. personal computers) so long as they provide similar functionality.

Also coupled to LAN 1 is a file server 62 and associated storage device, here a disc storage device 64. File server 62 provides controlled access by workstations 2, 22, 32, 34, and 85 to write information to and to read information from disc storage device 64.

Optionally, interfaces (not shown) may be used to couple various peripherals to LAN 1. For example, remote access modems may be coupled to one of such interfaces to provide access to the system from remote terminals (not shown) located elsewhere in the hospital or located off-site, such as at a physician's office or residence. Remote access may also be employed to diagnose system problems from an off-site facility. A laboratory system may be connected to an interface to permit the communication of laboratory information between the laboratory system and the clinical management system. An order communication system may be coupled to an interface to permit orders to be communicated from the system to other hospital systems (e.g. pharmacy or laboratory) and vice versa. An archival storage device may be coupled to an interface to permit any information stored in the system to be archived on suitable media, such as magnetic tapes or optical discs.

Printers 81 and 83 are coupled to file server 62 to allow patient information to be printed for the convenience of hospital personnel and to maintain a suitable legal record of all observations, orders, parameter readings, care plans, and other pertinent information regarding the monitored patients. Printers 81 and 83 may be any suitable printers such as, for example, laser printers or high speed dot matrix printers. A printer may optionally be coupled to the bedside terminal and/or the terminal at the nursing station or lounge, if desired.

During operation, the system user, typically a nurse or physician, conducts a dialog with the system through the use of a keyboard, mouse, light-pen, touch-pad, trackball, or other appropriate means for entering information. "Icons", screen-sensitive areas, or the equivalent, or any combination thereof which is appropriate to the end application, may also be provided.

The user provides information to or queries the system by means of the keyboard and/or pointing device, and receives information from the system by means of information displayed on the screen and/or through audible signals which could include speech synthesis.

Figure 2:
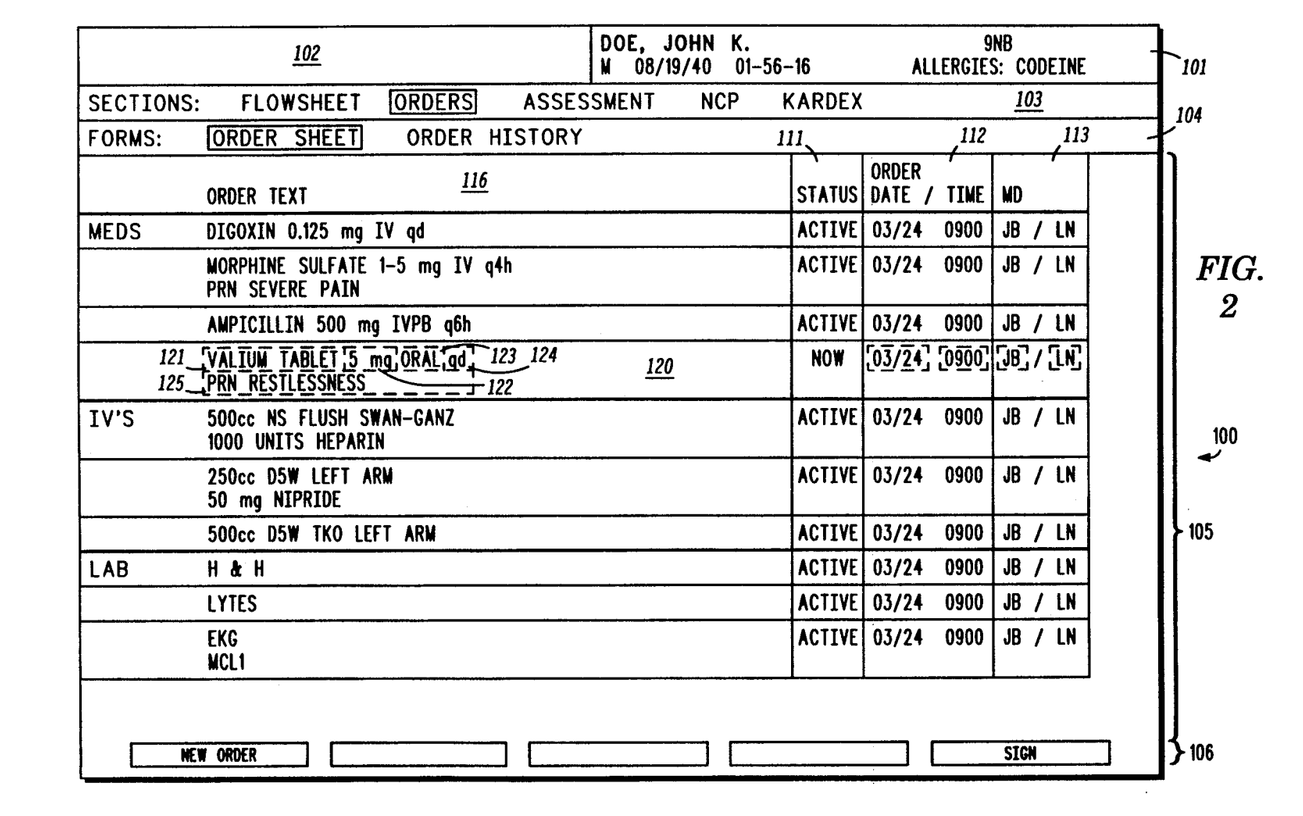
FIG. 2 is an information screen representing an ORDER SHEET form in an ORDERS section of a patient record.

Referring now to FIG. 2, an information screen, generally designated 100, is illustrated. Information screen 100 is an ORDER SHEET form from the ORDERS section of a patient record. Screen 100 generally consists of a patient demographics area 101, a message area 102, a sections area 103, a forms area 104, a display area 105, and a softkey area 106.

Figure 3:
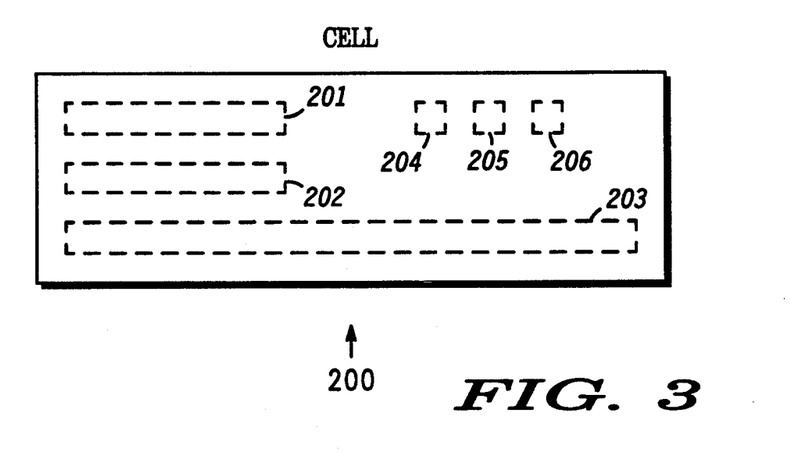
FIG. 3 is a cell of a screen, such as the information screen of FIG. 2, embodying the present invention.

In the order sheet displayed in area 105, columns 110-113 are column parameters provided for the order text, status of the order, order data/time, and the doctor placing the order, respectively. The blocks below column headings 110-113 are data cells. A basic data cell, generally designated 200, is illustrated in FIG. 3.

Cell 200 has several designated fields within the cell for displaying information. There are three basic types of information fields in cell 200: mandatory information fields designated by dashed lines 201 and 202; optional information fields designated by dashed line 203; and notational information fields designated by dashed lines 204-206.

Figure 4:
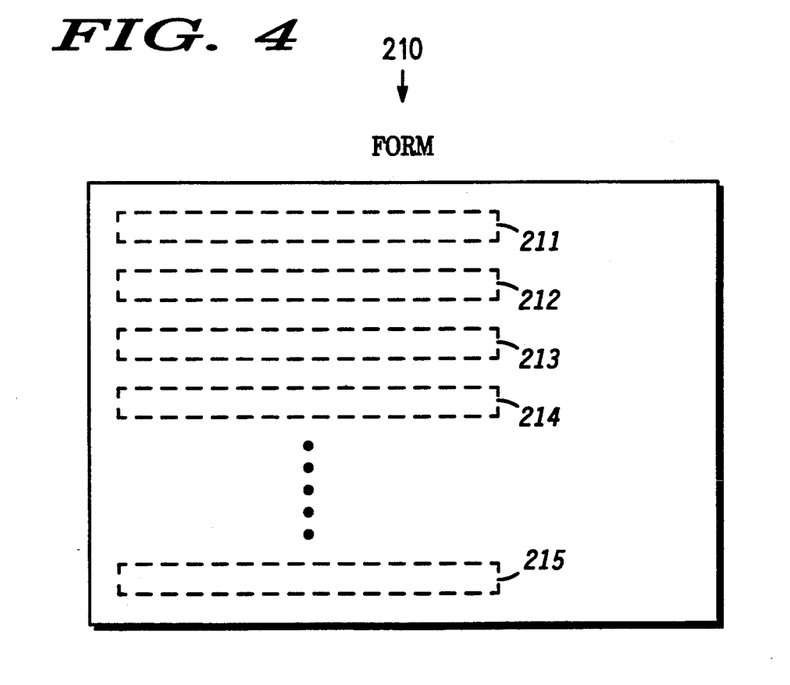
FIG. 4 is a form associated with a cell embodying the present invention.

In FIG. 4, a form, generally designated 210, is illustrated. Form 210 contains various information fields 211-215. The information in form 210 corresponds to attributes from one or more object instances.

As shown in cell 120 of FIG. 2, there are several data fields 121-125. Fields 121-124 are mandatory information fields and field 125 is an optional information field. By selecting cell 120, the form, generally designated 300, associated with cell 120 may be displayed, FIG. 10. Form 300 contains a label field 301 and various information fields 302-311. Mandatory, optional, and notational data fields and the relation of cell fields to attributes of object instances are described in more detail in copending patent application "Spreadsheet Cell having Multiple Data Fields" and "Electronic Data Storage Interface", identified above.

Figure 5:
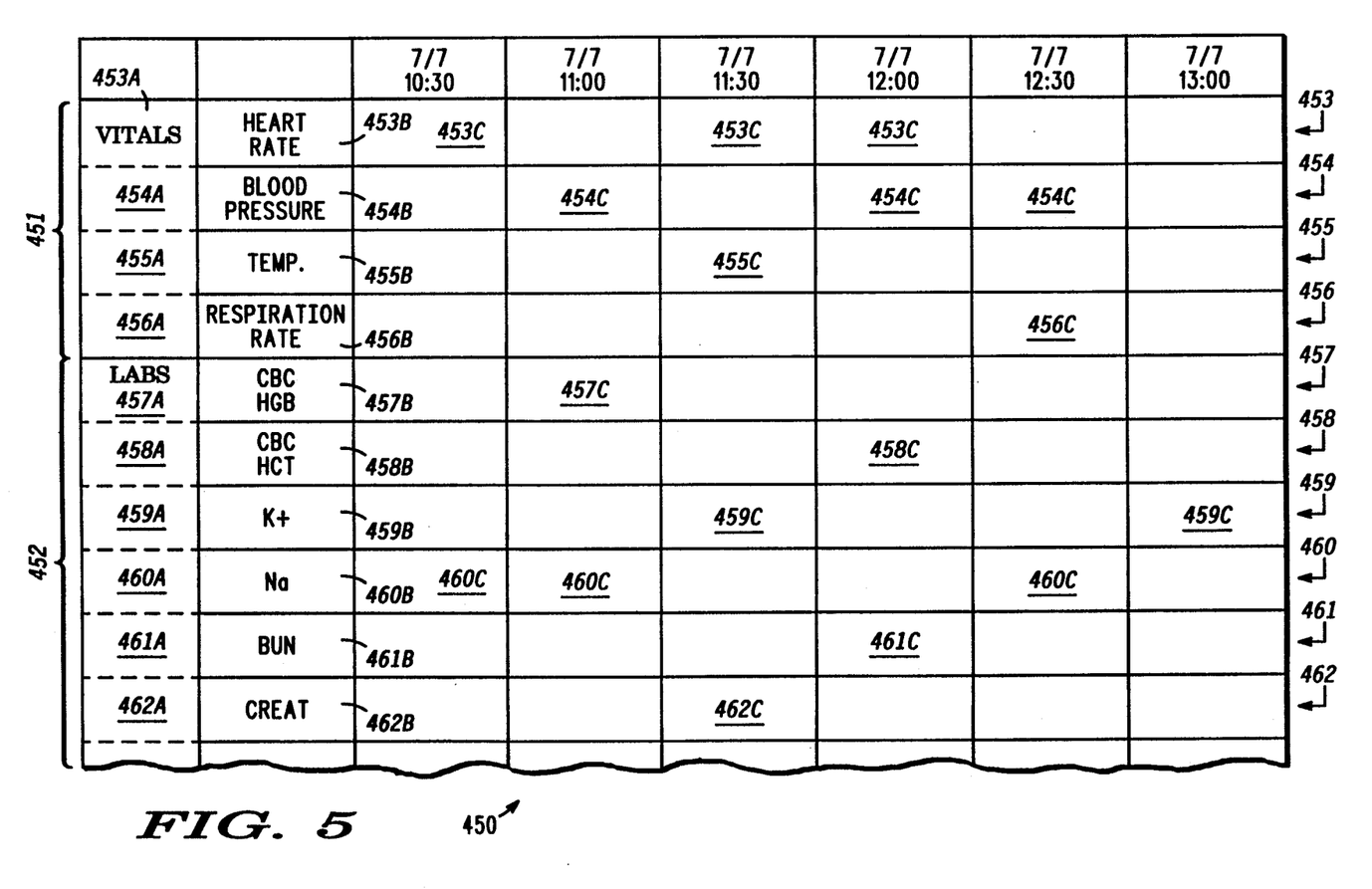
FIG. 5 is a display area portion of an information screen showing a VITALS group and a LABS group of a FLOWSHEET section of a patient record.

Referring now to FIG. 5, a display area portion of an information screen showing a vitals group 451 and a labs group 452 of a patient record is illustrated. Each group is further divided into several tiles. Vitals group 451 is divided into tiles 453-456 which correspond to vitals parameters: heart rate; blood pressure, temperature, and respiration rate, respectively. Labs group 452 is divided into tiles 457-462 which correspond to labs parameters CBC HGB, CBC HCT, K+, Na, BUN, and CREAT, respectively.

Form 450 is also divided into several columns. The first column, a group column, contains group cells 453A-462A. Of these, only cells 453A and 457A are utilized to show the group divisions. The second column, a parameter column, contains parameter cells 453B-462B. Each of these parameter cells is utilized to indicate the parameter for which the data cells contain information. The remaining columns are comprised of data cells 453C-462C arranged in relation to time intervals.

Figure 6:
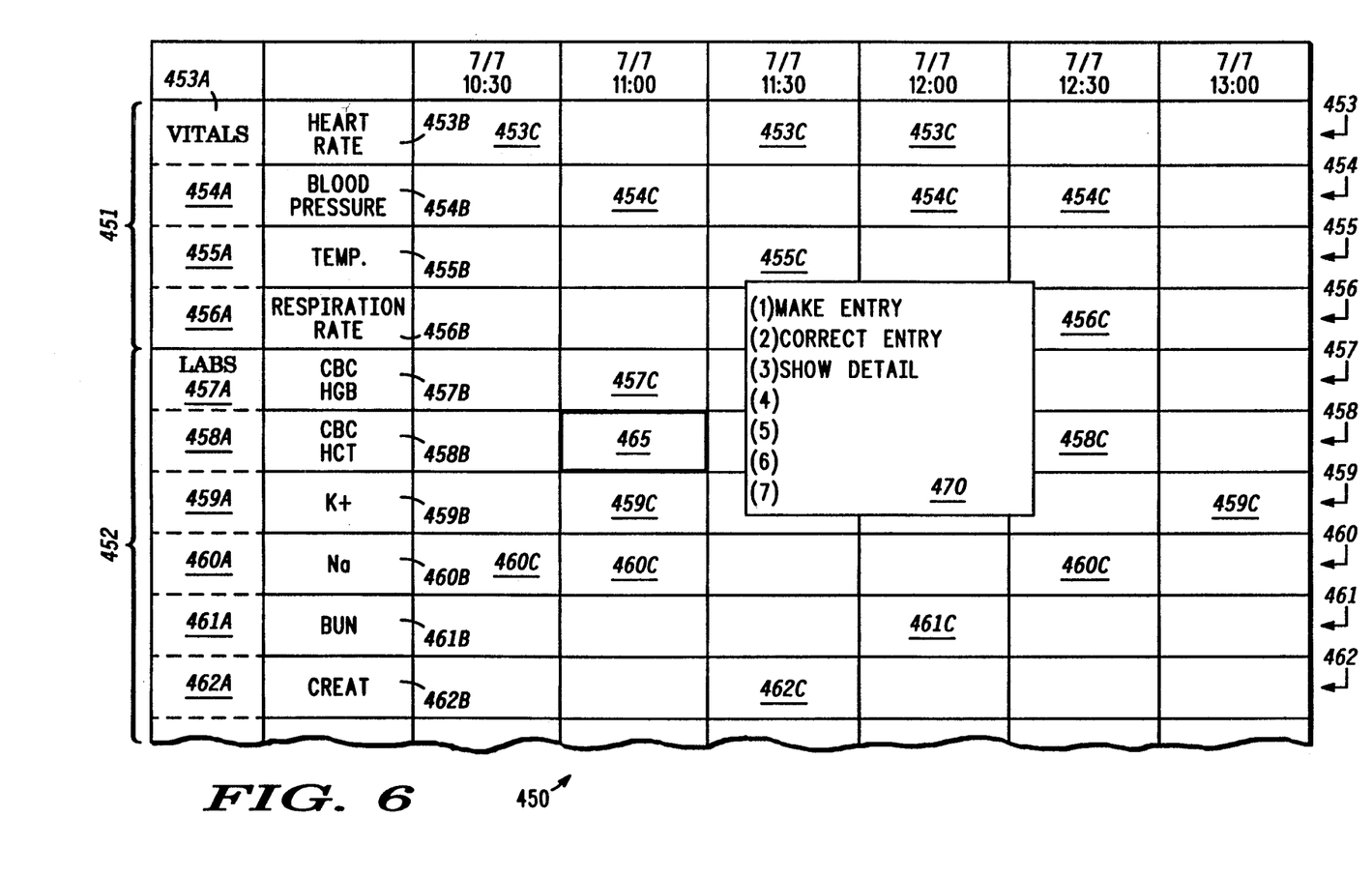
FIG. 6 is the display area of FIG. 5 with a pop-up window which appears upon selection of a data cell.

Referring now to FIG. 6, form 450 of FIG. 5 is illustrated with a pop-up window 470 which appears upon selection of a data cell, such as data cell 465. Generally, window 470 will provide three main options: making an entry, correcting an entry, and showing detail of the data cell.

Figure 7:
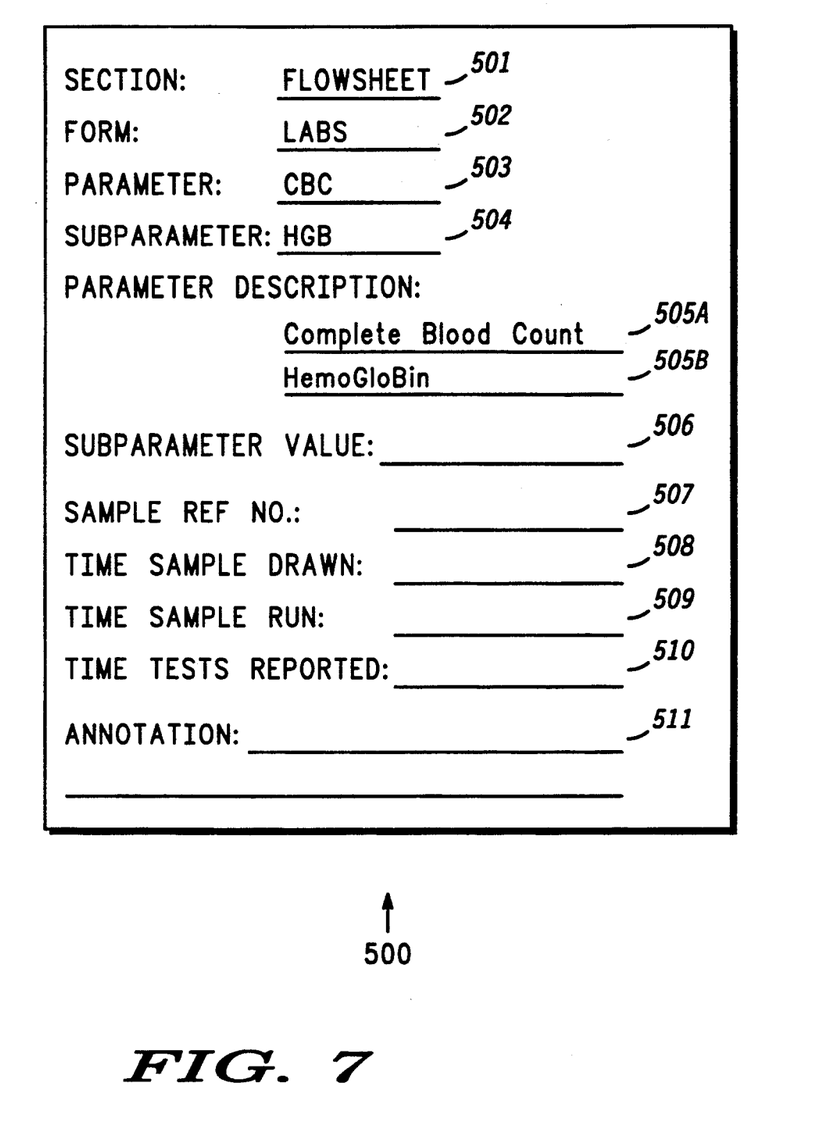
FIG. 7 shows a form associated with a data cell of the LABS form of FIG. 6.

When the show detail option is selected from the pop-up window, a form 500 of FIG. 7 appears. Form 500 has data fields for several pieces of information. An example of the information contained in form 500 consists of: a section name 501, a form name 502, a parameter name 503, a subparameter name 504, and a parameter description 505A and 505B. In addition, other items such as: a subparameter value 506, a sample reference number 507, a time the sample was drawn 508, a time the sample was run 509, and a time the test results were reported 510, are also shown. Generally, each form will also have an annotation (or comment) field 511.

In this particular case, the information for data fields 501-511 is generally not entered directly into form 500, although this is possible. The information for form 500 is obtained from a secondary form 600 illustrated in FIG. 8.

Figure 8:
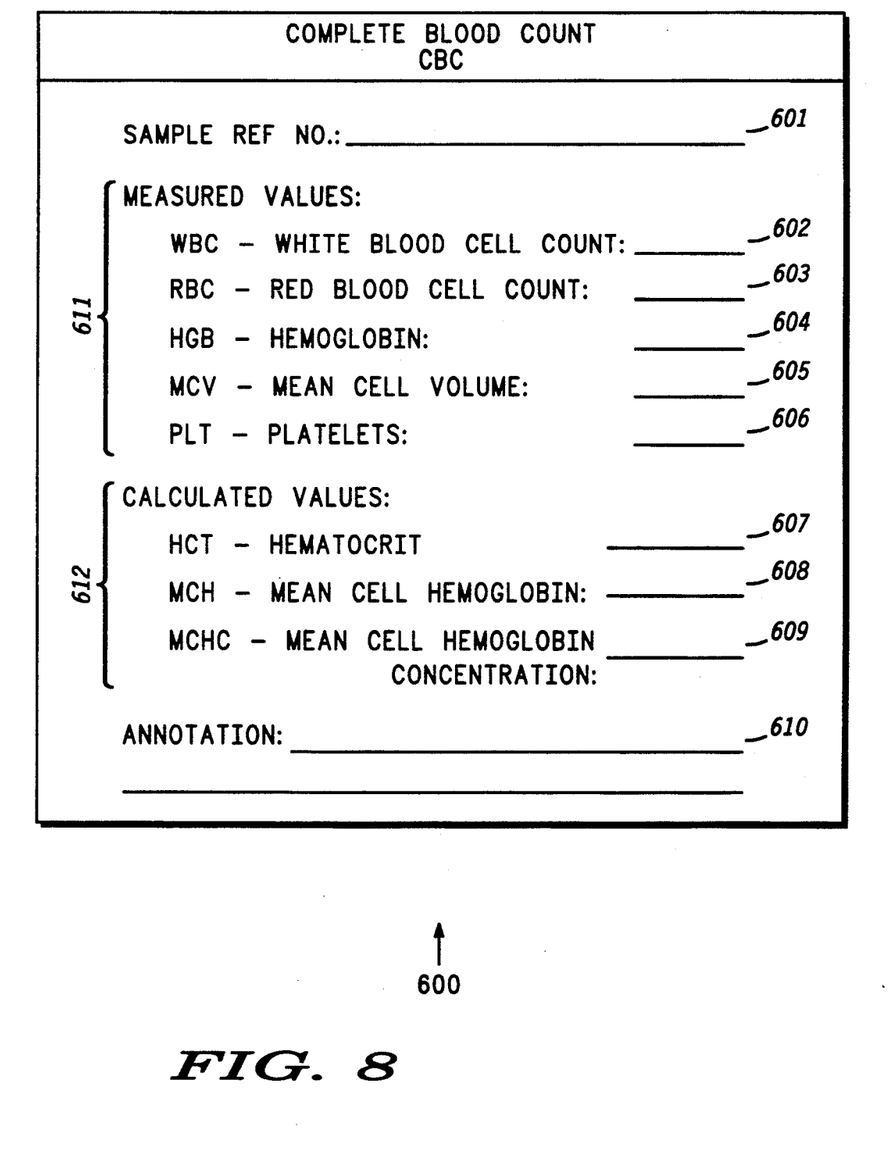
FIG. 8 shows a secondary form associated with the primary form of FIG. 7.

As shown in FIG. 8, secondary form 600 is for the complete blood count parameter. This particular parameter is not a value itself but comprises a series of subparameters. The subparameters are listed in rows consisting of: a WBC (White Blood Count) 602, a RBC (Red Blood Count) 603, a HGB (HemoGloBin) 604, a MCV (Mean Cell Volume) 605, a PLT (PLaTeletes) 606, an HCT (HematoCriT) 607, an MCH (Mean Cell Hemoglobin) 608, and an MCHC (Mean Cell Hemoglobin Concentration) 609. It should be noted that this list of CBC subparameters is not all inclusive, but is merely meant as an example.

Subparameters 602-609 are divided into two general groups: a measured group 611 and a calculated group 612. The measured group values are generally obtained by testing, manually or automatically. The calculated group values are derived from the measured group values. It should be understood that depending on the equipment used, some of the values could be placed in either group.

Other fields contained in secondary form 600 include a sample reference number 601 and an annotation field 610.

The parameter field 503, subparameter field 504 and value field 506, of FIG. 7, are obtained from the header and field 604 of FIG. 8.

Figure 9:
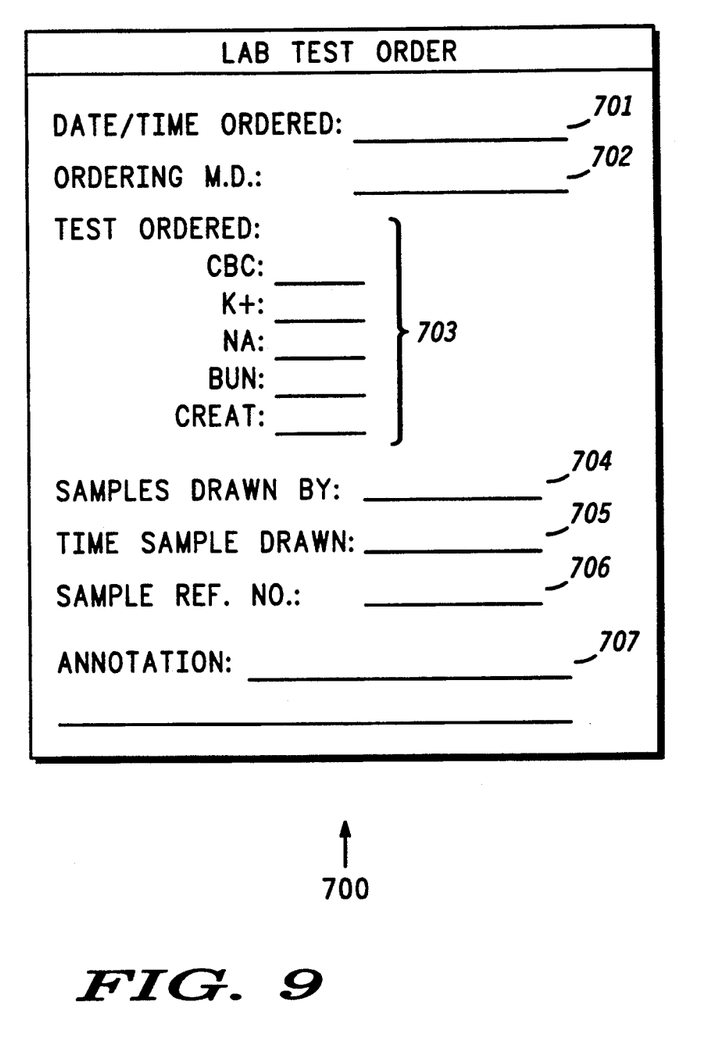
FIG. 9 shows a tertiary form associated with the secondary form of FIG. 8.

Again, many of the field values of secondary form 600 may be obtained from a tertiary form 700 shown in FIG. 9. Tertiary form 700 contains several fields which relate to secondary form 600. These fields consist of a time sample drawn field 705 and a sample reference number 706. Other fields included in form 700 are: a data/time order 701, an ordering MD 702, a listing of tests ordered 703, a sample drawn by 704, and an annotation 707.

Figure 11:
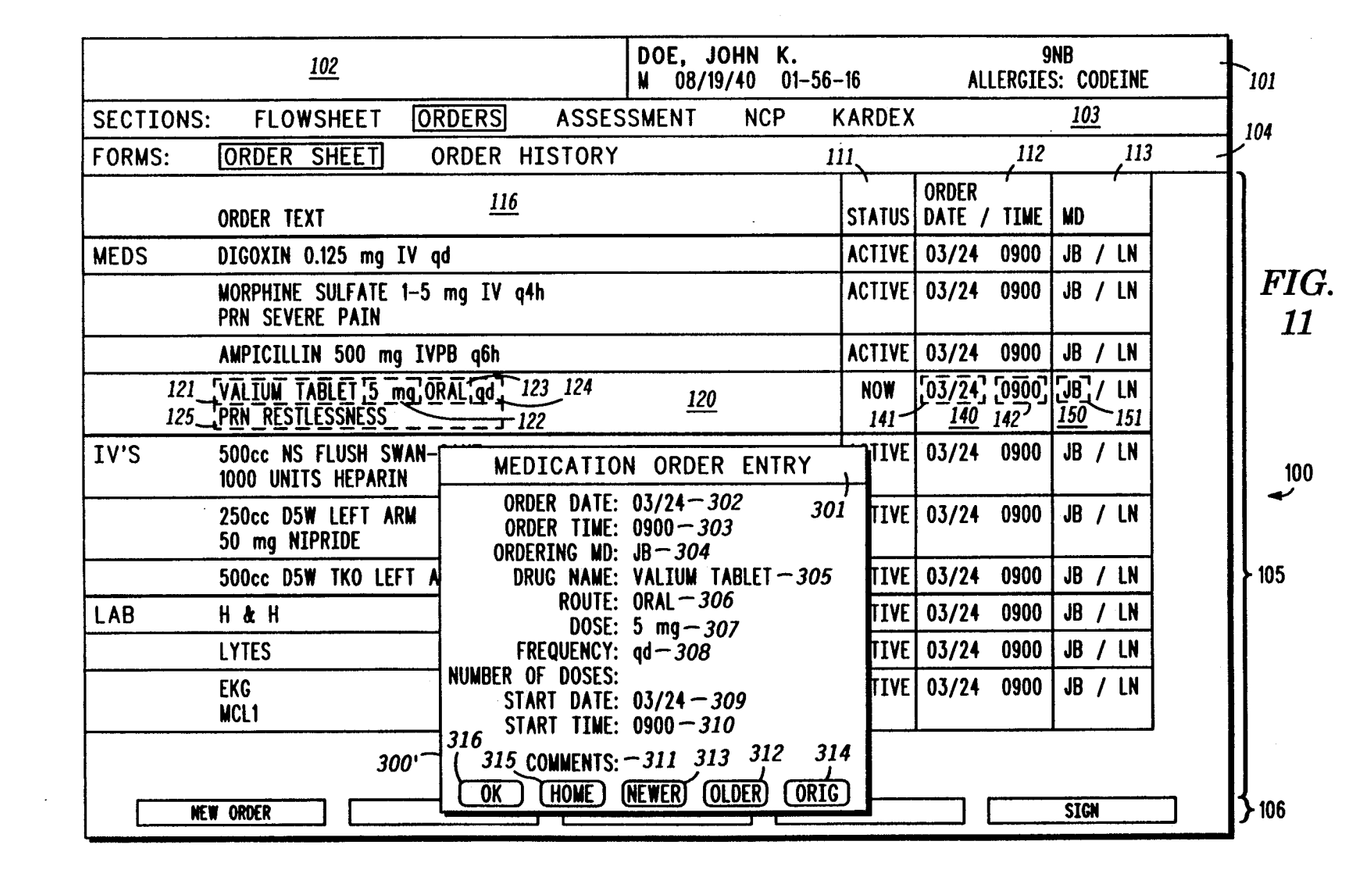
Figure 12:
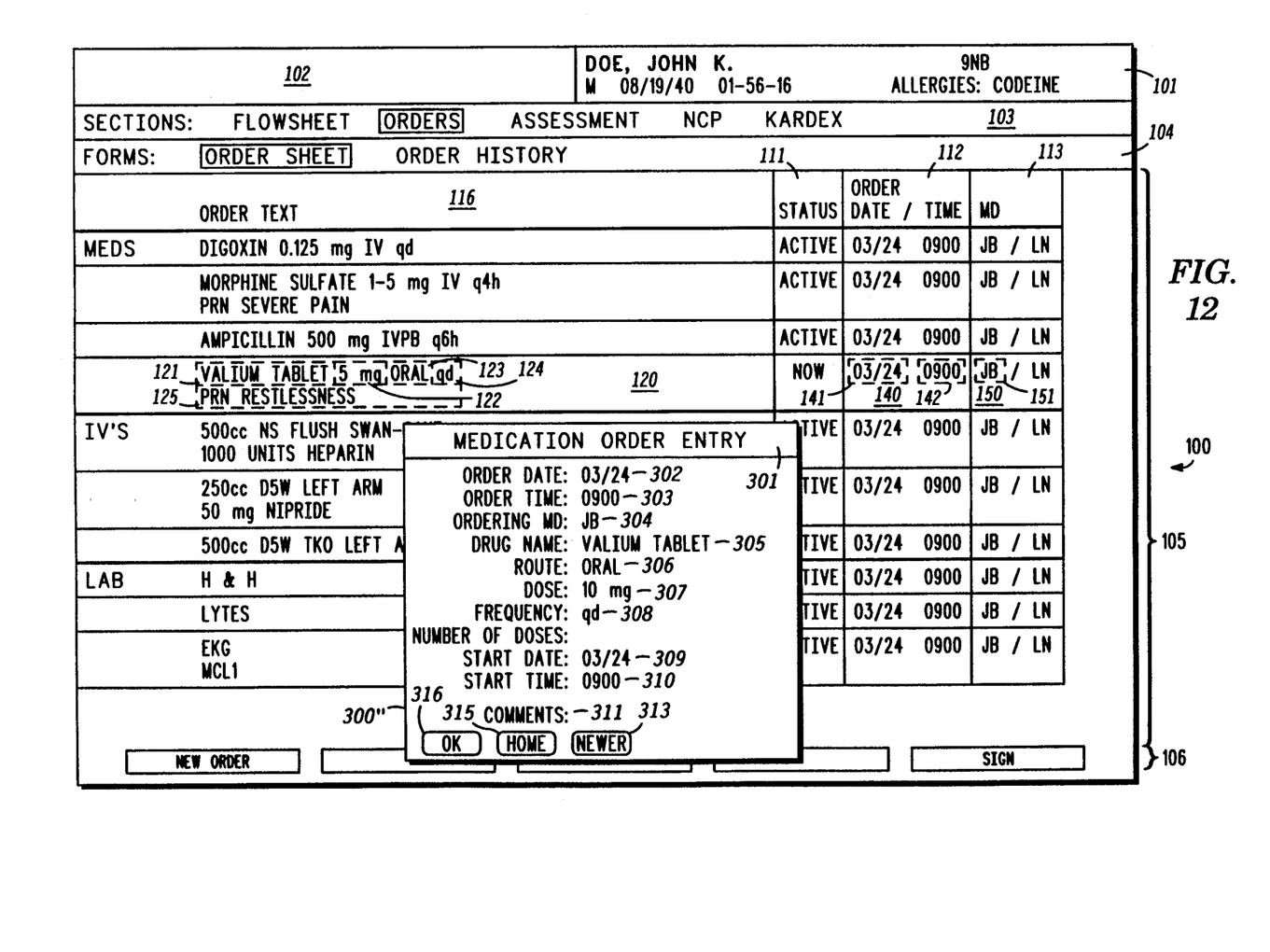

Referring now to FIGS. 10-12, a form 300 associated with cell 120 of FIG. 2 is illustrated. Here, a change and/or correction has been made to some information of a previous entry which was displayed in form 300. This is indicated by the appearance of an OLDER button 312. By selecting button 312, a previous form 300', FIG. 11, as it appeared before modification, is illustrated. It would also be possible to provide the previous button as a soft key in area 106 of the display.

As shown, form 300' did not have a comment entered at that time. The comment was added later and therefor, would be considered a change. As illustrated, form 300' has two buttons, OLDER button 312 which indicates that there are older changes to attributes of one or more object instances associated with form 300'; and a NEWER button 313 which is used to indicate that there are newer changes to attributes of one or more object instances associated with form 300'.

When OLDER button 312 of form 300' is selected, form 300" is presented, FIG. 12. As shown, form 300" differs from form 300' in the dose field 307. The dose was originally entered as 10 mg in form 300" and later corrected to 5 mg in form 300'. A change in this type of field would normally be considered a correction rather than a change.

Form 300" is shown with only a NEWER button 313. This is because form 300" is the view of the original object instance (i.e. there were no changes prior to this point).

Another button provided on each form is an "OK" button 316. The "OK" button permits the user to remove the form from the screen.

It would also be possible to add other buttons. Buttons such as ORIG button 314, FIGS. 10 and 11, which would bring up a form having the original attributes of the associated object instances. Another button which may be provided is a HOME button 315, FIGS. 11 and 12, which would bring up a form associated with the current cell display.

In addition, it would be possible, as discussed above, to identify the data which had been modified by displaying the modified data in a different font, a different color, blinking text, etc.

Figure 13A:
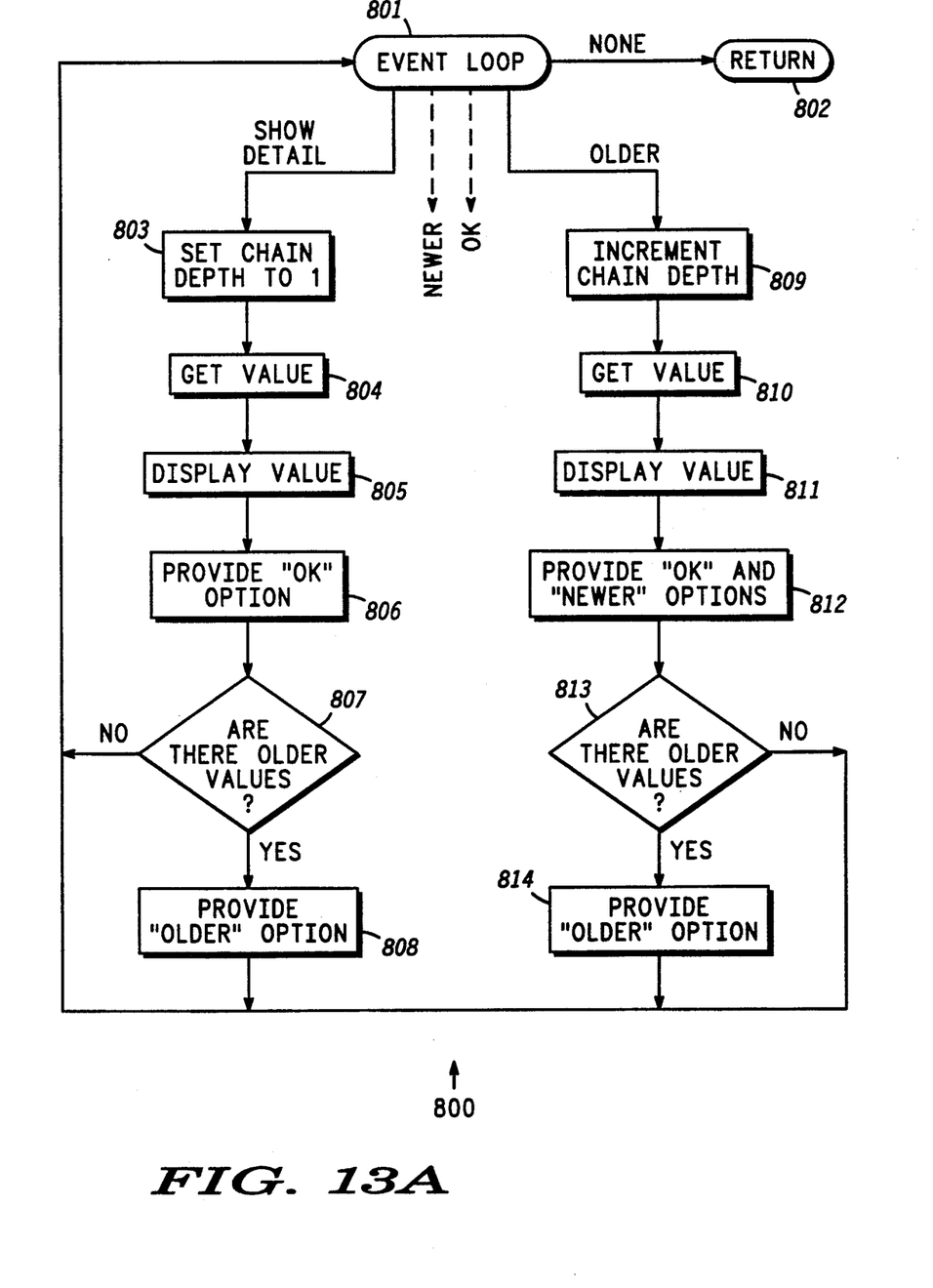
FIGS. 13A and 13B are graphical representations of a flowchart embodying the present invention.
Figure 13B:
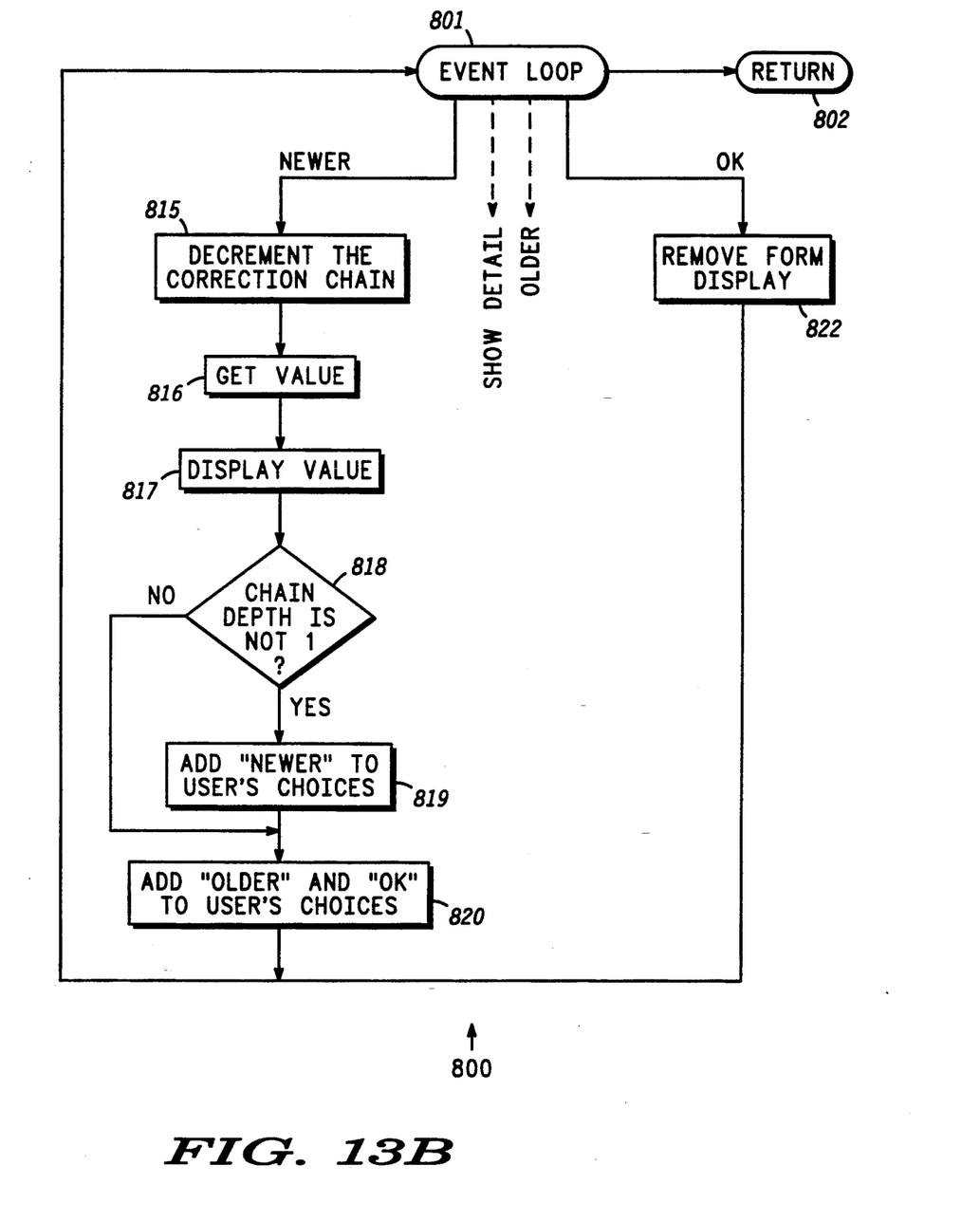

Referring now to FIGS. 13A and 13B, a flow chart, generally designated 800, illustrating a method embodying the present invention is shown. In addition, pseudo code for flowchart 800 is illustrated in Appendix A. The process commences at step 801 where it determines if an event has occurred. If no event has occurred, the process returns, step 802.

If a "Show Detail" option is selected, process 801 moves to step 803 where the chain depth is set to "1". The value is then obtained, step 804, and displayed, step 805.

An "OK" option is then provided for selection on the display, step 806. The process then moves to decision step 807 and determines if there are any older remaining values in the chain. If there are no older values, the process returns to step 801. If there are older values, an "Older" option is provided on the display.

If an "Older" option is available and selected, the process moves from step 801 to step 809, where the chain depth is incremented. The value is then retrieved, step 801, and displayed, step 811. The "OK" option is provided (as in step 806) along with a "Newer" option.

The process then moves to a decision step 813 and determines if there are any older remaining values in the chain. If there are no older values, the process returns to step 801. If there are older values, the "Older" option is provided on the display.

If a "Newer" option is available and selected, the process moves from step 801 to 815, where the chain depth is decremented. The value is then retrieved, step 816, and displayed, step 817.

The option then moves to a decision step 818 where it determines whether the chain depth is not equal to "1". If the chain depth is not equal to "1", the process moves to step 819 where a "Newer" option is provided. Following step 819, or if the chain depth is equal to "1", the process moves to step 820 where the "Older" and "OK" options are provided. The process then returns to step 801.

If the "OK" option is present and selected, the process moves from step 801 to step 822, where the form is removed. The process then returns to step 801.

Therefore, a method has been shown which accomplishes the objectives of displaying information from an information based computer system which consolidates information from various object instances to be displayed onto a single form. Additionally, the system maintains an historical record of changes/corrections to the object instances.

Thus, it will be apparent to one skilled in the art that there has been provided in accordance with the invention, a data cell that fully satisfies the objects, aims, and advantages set forth above.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

APPENDIX A

Loop waiting for events:
  Case Event "Show Detail"
    Get the value on the correction chain at current depth.
    Display a new form with the correction value in the field.
    Add "OK" to the user's choices.
    If there are older corrections on the correction chain:
      Add "Older" to the user's choices.
  Case Event "Older":
    Increment the chain depth.
    Get the value on the correction chain at current depth.
    Display the correction value in the current form's field.
    Add "Newer" and "OK" to the user's choices.
    If there are older corrections on the correction chain:
      Add "Older" to the user's choices.
  Case Event "OK"
    Remove the form.
    Case Event "Newer"
      Decrement the chain depth.
      Get the value on the correction chain at the current depth.
      Display the correction value in the current form's field.
      If the chain depth is not one:
        Add "Newer" to the user's choices.
      Add "Older" and "OK" to the user's choices.
  Case Default
    Handle other events.
End of loop

We claim:

1. A method for displaying information from an information based computer system, said system having a means for displaying said information and a means for storing said information, said method comprising the steps of:
    receiving an instruction to display a first data value in a cell;
    initializing a data value depth counter; and
    displaying said first data value associated with said data value depth counter in said cell.

2. The method of claim 1 further comprising the step of providing a user option to remove the display of said first data value.

3. The method of claim 1 further comprising the steps of:
    determining if there is a first previous data value linked to said first data value in said means for storing said information; and
    providing a user option to display said first previous data value.

4. A method for displaying information from an information based computer system, said system having a means for displaying said information and a means for storing said information, said method comprising the steps of:

displaying a first data value in a cell;
receiving an instruction to display a first previous data value in said cell;
incrementing a data value depth counter; and
displaying said first previous data value in said cell.

5. The method of claim 4 further comprising the step of providing a user option to remove the display of said first previous data value.

6. The method of claim 4 further comprising the step of providing a user option to retrieve said first data value.

7. The method of claim 6 further comprising the steps of:

decrementing said data value depth counter; and
displaying said first data value.

8. The method of claim 4 further comprising the steps of:

determining if there is a second previous data value linked to said first previous data value; and
providing a user option to display said second previous data value.

9. A method for displaying information from an information based computer system, said system having a means for displaying said information and a means for storing said information, said method comprising the steps of:

displaying a data value in a cell;
decrementing a data value depth counter;
receiving an instruction to display a first subsequent data value in said cell; and
displaying said first subsequent data value.

10. The method of claim 9 further comprising the step of providing a user option to remove the display of said first subsequent data value.

11. The method of claim 9 further comprising the step of providing a user option to display a first previous data value.

12. The method of claim 11 further comprising the steps of:

incrementing said data value depth counter; and
displaying said first previous data value.

13. The method of claim 9 further comprising the steps of:

determining if said data value depth counter is equal to a depth of said data value; and
providing a user option to display a second subsequent data value if said data value depth counter is not equal to a depth counter value for said data value.

* * * * *